US00PP09445P

United States Patent [19]

VandenBerg

[11] Patent Number: Plant 9,445

[45] Date of Patent: Jan. 30, 1996

[54] CHRYSANTHEMUM PLANT NAMED 'STEPHANIE'

[75] Inventor: Cornelis P. VandenBerg, Salinas, Calif.

[73] Assignee: Yoder Brothers, Inc., Barberton, Ohio

[21] Appl. No.: 367,571

[22] Filed: Dec. 30, 1994

[51] Int. Cl.[6] ..... A01H 5/00

[52] U.S. Cl. ..... Plt./82.1

[58] Field of Search ..... Plt./82.1, 76

[56] References Cited

U.S. PATENT DOCUMENTS

P.P. 6,058 12/1987 Duffett ..... Plt./82.1

P.P. 7,885 6/1992 Fuess ..... Plt./82.1

*Primary Examiner*—Howard J. Locker

*Attorney, Agent, or Firm*—Foley & Lardner

[57] ABSTRACT

A Chrysanthemum plant named Stephanie particularly characterized by its flat capitulum form; daisy capitulum type; white ray floret color; diameter across face of capitulum of 58 to 61 mm when fully opened; branching pattern is spreading and prolific; natural season flower date of September 14 to 22 when planting rooted cuttings on June 11 to June 18 in Hightstown, N.J.; plant height of 25 to 30 cm when grown in fall under natural daylength with no growth regulators in New Jersey; excellent uniform growth habit; and good flexibility of plant for handling, packing and shipping.

3 Drawing Sheets

The present invention comprises a new and distinct cultivar of Chrysanthemum, botanically known as *Dendranthema grandiflora,* and referred to by the cultivar name Stephanie.

Stephanie, identified as 8773 (90-670001), was originated from an open pollination of parents selected by Cornelis P. VandenBerg in a controlled breeding program in Salinas, Calif., in 1989.

The female parent of Stephanie was an unnamed seedling identified as 9430 (88-336001) and described as a flat daisy garden mum with yellow ray floret color.

The male parent of Stephanie was unknown, since the breeding program consisted of open pollinated females.

Stephanie was discovered and selected as one flowering plant within the progeny of the stated cross by Cornelis P. VandenBerg in November 1990, in a controlled environment in Salinas, Calif.

The first act of asexual reproduction of Stephanie was accomplished when vegetative cuttings were taken from the initial selection in January 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Stephanie are firmly fixed and are retained through successive generations of asexual reproduction.

Stephanie has not been observed under all possible environmental conditions. The phenotype may vary significantly with variations in environment such as temperature, light intensity and daylength, without, however, any variance in genotype.

The following observations, measurements and comparisons describe plants grown in controlled open areas in Hightstown, N.J. Rooted cuttings were established in soil and maintained outdoors under the natural temperature and daylength prevailing during June through October.

The following traits have been repeatedly observed and are determined to be basic characteristics of Stephanie, which, in combination, distinguish this chrysanthemum as a new and distinct cultivar:

1. Flat capitulum form.
2. Daisy capitulum type.
3. White ray floret color.

4. Diameter across face of capitulum of 58 to 61 mm when fully opened.
5. Branching pattern is spreading and prolific.
6. Natural season flower date of September 14 to 22 when planting rooted cuttings on June 11 to June 18 in Hightstown, N.J.
7. Plant height of 25 to 30 cm when grown in fall under natural daylength with no growth regulators in New Jersey.
8. Excellent uniform growth habit.
9. Good flexibility of plant for handling, packing and shipping.

The accompanying photographic drawings show typical inflorescence and leaf characteristics of Stephanie, with the colors being as nearly true as possible with illustrations of this type.

Sheet 1 is a color photograph of Stephanie grown as a pinched garden mum under natural season outside conditions in Salinas, Calif. Plants were grown outside and dug and transplanted into 15 cm pots at flowering time for photography purposes.

Sheet 2 is a black and white photograph of three views of the inflorescence of Stephanie.

Sheet 3 is a black and white photograph showing the upper and under sides of the leaves of Stephanie at three stages of development (mature, intermediate and immature). In sheets 2 and 3 a measuring tape in centimeters has been added.

Of the commercial cultivars known to the inventor, the most similar in comparison to Stephanie is the cultivar Tracy, disclosed in U.S. Plant Pat. No. 8,609. Reference is made to attached Chart A, which compares certain characteristics of Stephanie to the same characteristics of Tracy.

Similar traits are ray floret color, capitulum form and type, and branching pattern. Stephanie has in general a smaller diameter of capitulum than Tracy. Stephanie has a much earlier natural season flowering date and has a shorter plant height when compared with Tracy.

In the following description, color references are made to The Royal Horticultural Society Colour Chart. The color values were determined on plant material grown as a pinched garden mum grown outdoors in Salinas, Calif. on Aug. 21, 1994.

Classification

*Botanical.—Dendranthema grandiflora,* cv., Stephanie.

*Commercial.*—Flat daisy garden mum.

INFLORESCENCE

Capitulum:

*Form.*—Flat.

*Type.*—Daisy.

*Diameter across face.*—58 to 61 mm when fully opened.

Corolla of ray florets:

*Color (general tonality from a distance of three meters).*—White.

*Color (upper surface).*—155B. Immature petals closest to 4D.

*Color (under surface).*—155B.

*Shape.*—Cross section convex, longitudinal section straight.

Corolla of disc florets:

*Color (mature).*—14A.

*Color (immature).*—14A, tinged with 144C.

Reproductive organs:

*Androecium.*—Present on disc florets only; moderate pollen.

*Gynoecium.*—Present on both ray and disc florets.

PLANT

General appearance:

*Height.*—25 to 30 cm when grown in fall under natural daylength with no growth regulators in New Jersey.

*Branching pattern.*—Spreading and prolific.

Foliage:

*Color (upper surface).*—147A.

*Color (under surface).*—147B.

*Shape.*—Deeply lobed, serrated.

CHART A

COMPARISONS MADE OF PLANTS GROWN UNDER NATURAL SEASON OUTDOOR CONDITIONS HIGHTSTOWN, NEW JERSEY

| | STEPHANIE | TRACY |
|---|---|---|
| Ray floret color | White | White |
| Capitulum form and type | Flat, daisy | Flat, daisy |
| Diameter across face of capitulum | 58 to 61 mm | 54 to 70 mm |
| Branching pattern | Spreading and prolific | Spreading and prolific |
| Natural season flower date in Hightstown, NJ | Sept. 14 to 22 | Sept. 28 to Oct. 3 |
| Plant height in natural season fall | 25 to 30 cm | 30 to 36 cm |

It is claimed:

1. A new and distinct Chrysanthemum plant named Stephanie, as described and illustrated.

* * * * *

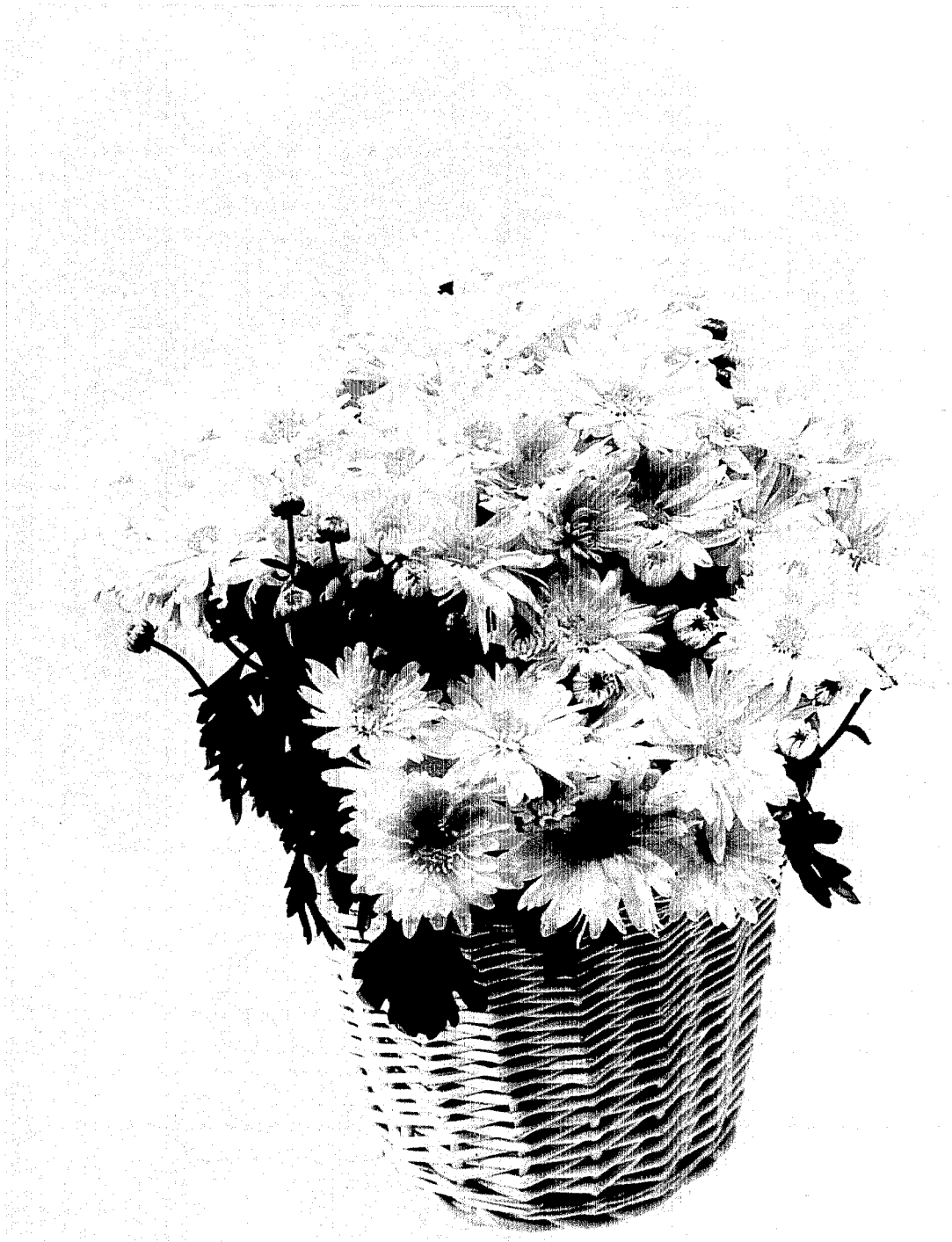

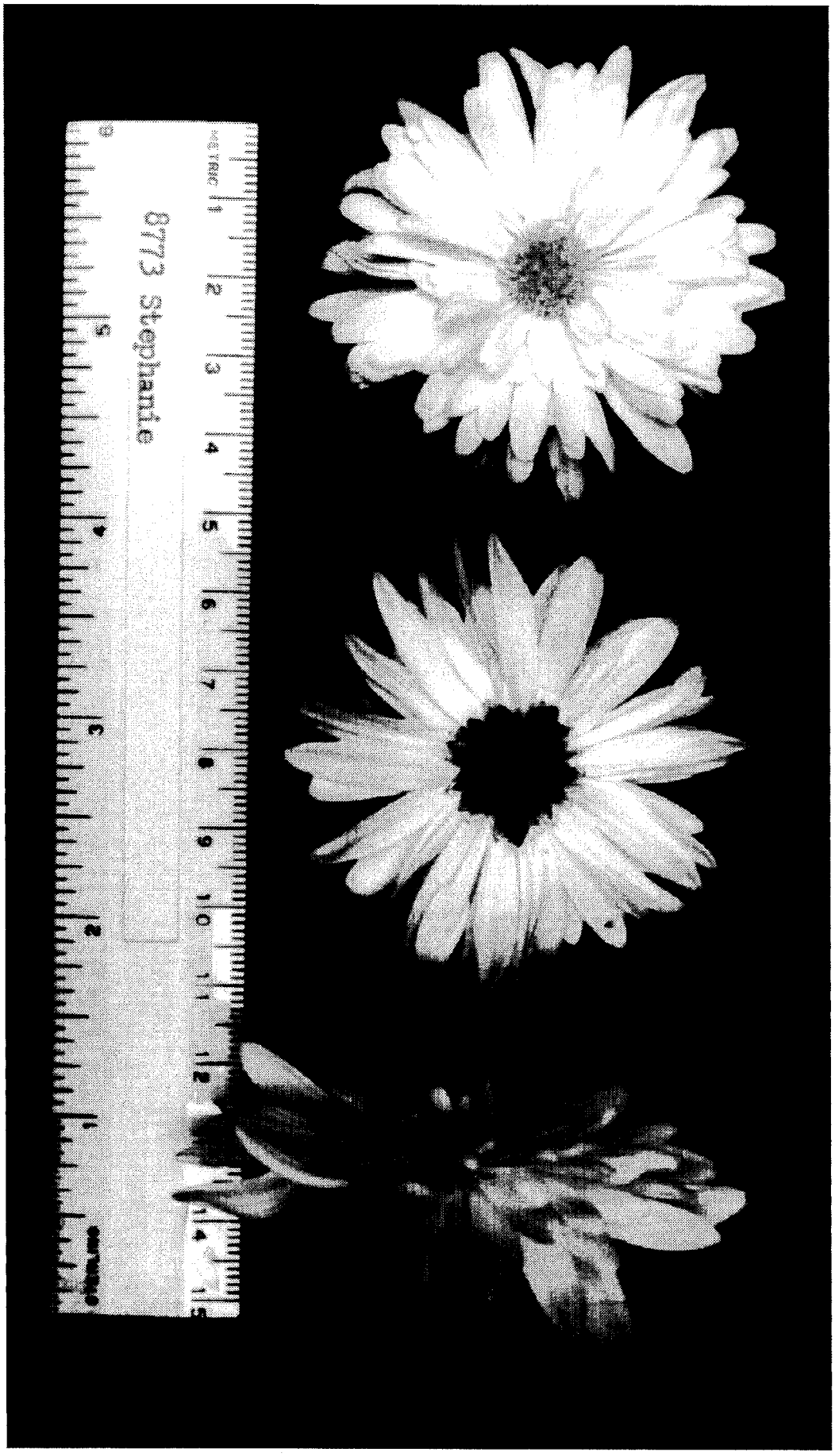
8773 Stephanie

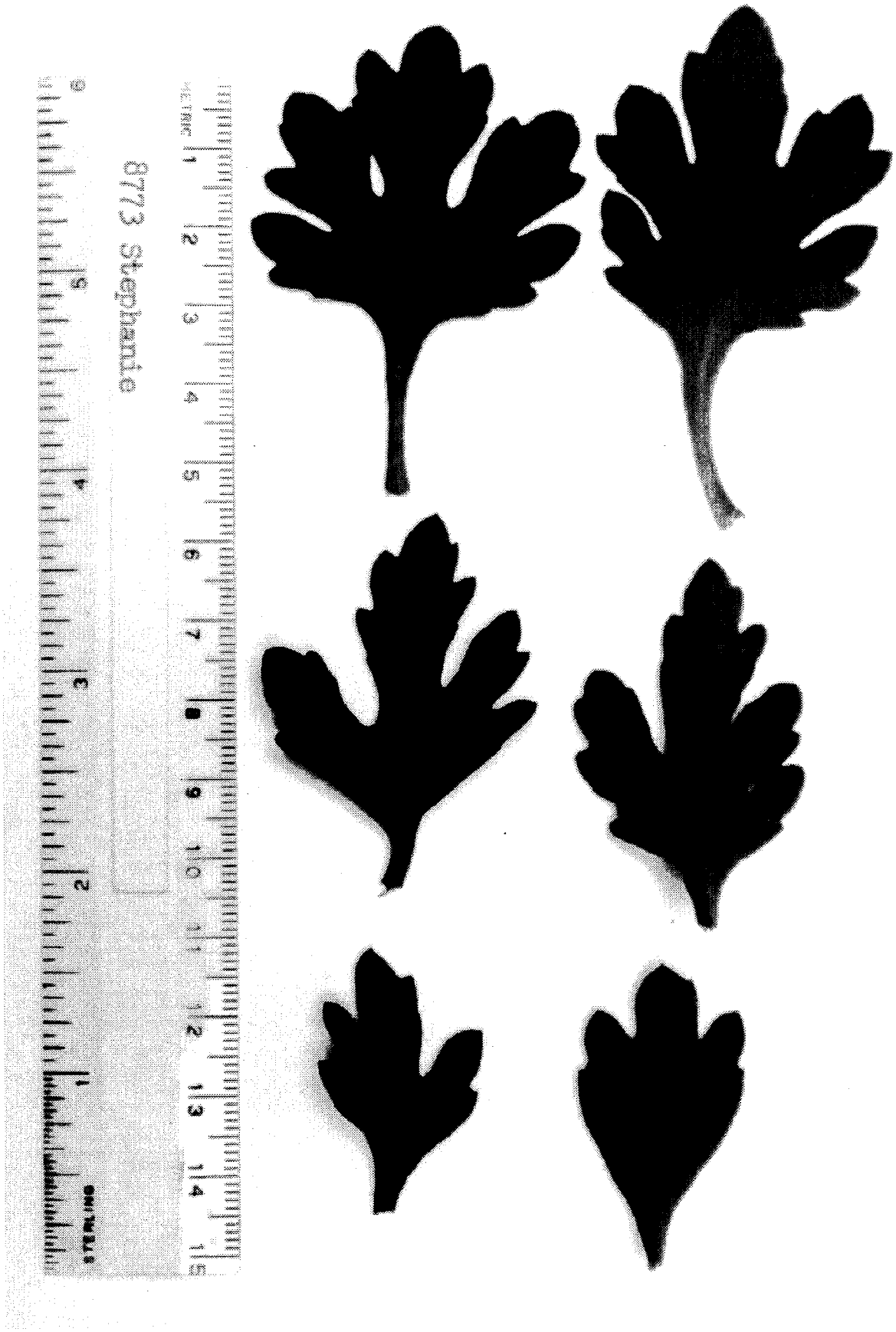
8773 Stephanie